United States Patent
Zhai et al.

(10) Patent No.: US 12,168,785 B2
(45) Date of Patent: Dec. 17, 2024

(54) RECOMBINANT KOD POLYMERASE

(71) Applicant: BGI SHENZHEN, Shenzhen (CN)

(72) Inventors: Lili Zhai, Shenzhen (CN); Lin Wang, Shenzhen (CN); Wenwei Zhang, Shenzhen (CN); Yuliang Dong, Shenzhen (CN); Yue Zheng, Shenzhen (CN); Fen Liu, Shenzhen (CN)

(73) Assignee: BGI SHENZHEN, Shenzhen (CN)

( * ) Notice: Subject to any disclaimer, the term of this patent is extended or adjusted under 35 U.S.C. 154(b) by 926 days.

(21) Appl. No.: 17/270,489

(22) PCT Filed: Sep. 3, 2018

(86) PCT No.: PCT/CN2018/103764
§ 371 (c)(1),
(2) Date: Feb. 23, 2021

(87) PCT Pub. No.: WO2020/047695
PCT Pub. Date: Mar. 12, 2020

(65) Prior Publication Data
US 2021/0324353 A1      Oct. 21, 2021

(51) Int. Cl.
*C12Q 1/68* (2018.01)
*C12N 9/12* (2006.01)
(Continued)

(52) U.S. Cl.
CPC ......... *C12N 9/1252* (2013.01); *C12Q 1/6806* (2013.01); *C12Q 1/6869* (2013.01); *C12Y 207/07007* (2013.01)

(58) Field of Classification Search
None
See application file for complete search history.

(56) References Cited

U.S. PATENT DOCUMENTS

| 6,602,695 B2 | 8/2003 | Patel et al. |
| 9,657,281 B2 * | 5/2017 | Vander Horn ....... C12N 9/1252 |

(Continued)

FOREIGN PATENT DOCUMENTS

| CN | 106536728 A | 3/2017 |
| CN | 107002051 A | 8/2017 |

(Continued)

OTHER PUBLICATIONS

Mar. 10, 2023, Office Action issued in EP Application No. 18932681.2.

(Continued)

*Primary Examiner* — Aaron A Priest
(74) *Attorney, Agent, or Firm* — Piloff Passino & Cosenza LLP; Rachel K. Pilloff; Sean A. Passino (57) ABSTRACT

Provided is a recombinant KOD polymerase, which is the following A) or B): the polymerase shown in A) is a protein having DNA polymerase activity that is obtained by modifying amino acid residues in at least one of the following 18 positions in a wild-type KOD DNA polymerase amino acid sequence: 675th, 385th, 710th, 674th, 735th, 736th, 606th, 709th, 347th, 349th, 590th, 676th, 389th, 589th, 680th, 384th, 496th and 383rd; the polymerase described by B) is a protein having DNA polymerase activity that is derived from A) by adding a tag sequence to an end of the amino acid sequence of the protein shown in A).

12 Claims, 1 Drawing Sheet
Specification includes a Sequence Listing.

Concentration of the substrate (51) Int. Cl.
*C12Q 1/6806* (2018.01)
*C12Q 1/6869* (2018.01)

(56) References Cited

U.S. PATENT DOCUMENTS

| | | | |
|---|---|---|---|
| 9,677,057 B2 | 6/2017 | Bomati et al. | |
| 9,765,309 B2 | 9/2017 | Chen et al. | |
| 10,662,413 B2 | 5/2020 | Lin Wu et al. | |
| 10,883,091 B2 | 1/2021 | Wang et al. | |
| 2007/0048748 A1* | 3/2007 | Williams | C12N 9/1252 435/6.12 |
| 2018/0119115 A1* | 5/2018 | Lin Wu | C12P 19/30 |

FOREIGN PATENT DOCUMENTS

| | | | | |
|---|---|---|---|---|
| CN | 108018270 A | 5/2018 | | |
| WO | WO-03060144 A2 * | 7/2003 | | C12N 9/1252 |

OTHER PUBLICATIONS

Jan. 18, 2023, Office Action issued in CN Application No. 201880096312.3.

Konrad Bergen et al., "Structures of KOD and 9° N DNA Polymerase Complexed with Primer Template Duplex," ChemBioChem, Jun. 2013, pp. 1,058-1,062, vol. 14.

Jun. 4, 2019, International Search Report of PCT/CN2018/103764.

Jun. 4, 2019, Written Opinion of the International Searching Authority of PCT/CN2018/103764.

Dunn, M.R. et al. "Exonuclease-Deficient DNA Polymerase [Expression Vector pGDR11—KOD]" Genbank Accession: ALL53339.1, Jan. 22, 2016.

Huber, C. et al. "Variants of Sequence Family B Thermococcus Kodakaraensis DNA Polymerase with Increased Mismatch Extension Selectivity" PLOS One, pp. 1-17, vol. 12, No. 8, Jan. 22, 2016.

* cited by examiner

SEQUENCE LISTING

<160> NUMBER OF SEQ ID NOS: 6

<210> SEQ ID NO 1
<211> LENGTH: 774
<212> TYPE: PRT
<213> ORGANISM: Artificial Sequence
<220> FEATURE:
<223> OTHER INFORMATION: Amino acid sequence of wild-type KOD DNA polymerase

<400> SEQUENCE: 1

```
Met Ile Leu Asp Thr Asp Tyr Ile Thr Glu Asp Gly Lys Pro Val Ile
1               5                   10                  15

Arg Ile Phe Lys Lys Glu Asn Gly Glu Phe Lys Ile Glu Tyr Asp Arg
            20                  25                  30

Thr Phe Glu Pro Tyr Phe Tyr Ala Leu Leu Lys Asp Asp Ser Ala Ile
        35                  40                  45

Glu Glu Val Lys Lys Ile Thr Ala Glu Arg His Gly Thr Val Val Thr
    50                  55                  60

Val Lys Arg Val Glu Lys Val Gln Lys Phe Leu Gly Arg Pro Val
65                  70                  75                  80

Glu Val Trp Lys Leu Tyr Phe Thr His Pro Gln Asp Val Pro Ala Ile
                85                  90                  95

Arg Asp Lys Ile Arg Glu His Pro Ala Val Ile Asp Ile Tyr Glu Tyr
            100                 105                 110

Asp Ile Pro Phe Ala Lys Arg Tyr Leu Ile Asp Lys Gly Leu Val Pro
        115                 120                 125

Met Glu Gly Asp Glu Glu Leu Lys Met Leu Ala Phe Ala Ile Ala Thr
130                 135                 140

Leu Tyr His Glu Gly Glu Glu Phe Ala Glu Gly Pro Ile Leu Met Ile
145                 150                 155                 160

Ser Tyr Ala Asp Glu Glu Gly Ala Arg Val Ile Thr Trp Lys Asn Val
                165                 170                 175

Asp Leu Pro Tyr Val Asp Val Val Ser Thr Glu Arg Glu Met Ile Lys
            180                 185                 190

Arg Phe Leu Arg Val Val Lys Glu Lys Asp Pro Asp Val Leu Ile Thr
        195                 200                 205

Tyr Asn Gly Asp Asn Phe Asp Phe Ala Tyr Leu Lys Lys Arg Cys Glu
    210                 215                 220

Lys Leu Gly Ile Asn Phe Ala Leu Gly Arg Asp Gly Ser Glu Pro Lys
225                 230                 235                 240

Ile Gln Arg Met Gly Asp Arg Phe Ala Val Glu Val Lys Gly Arg Ile
                245                 250                 255

His Phe Asp Leu Tyr Pro Val Ile Arg Arg Thr Ile Asn Leu Pro Thr
            260                 265                 270

Tyr Thr Leu Glu Ala Val Tyr Glu Ala Val Phe Gly Gln Pro Lys Glu
        275                 280                 285

Lys Val Tyr Ala Glu Glu Ile Thr Thr Ala Trp Glu Thr Gly Glu Asn
    290                 295                 300

Leu Glu Arg Val Ala Arg Tyr Ser Met Glu Asp Ala Lys Val Thr Tyr
305                 310                 315                 320

Glu Leu Gly Lys Glu Phe Leu Pro Met Glu Ala Gln Leu Ser Arg Leu
                325                 330                 335

Ile Gly Gln Ser Leu Trp Asp Val Ser Arg Ser Ser Thr Gly Asn Leu
            340                 345                 350
```

-continued

```
Val Glu Trp Phe Leu Leu Arg Lys Ala Tyr Glu Arg Asn Glu Leu Ala
            355                 360                 365

Pro Asn Lys Pro Asp Glu Lys Glu Leu Ala Arg Arg Gln Ser Tyr
        370                 375                 380

Glu Gly Gly Tyr Val Lys Glu Pro Glu Arg Gly Leu Trp Glu Asn Ile
385                 390                 395                 400

Val Tyr Leu Asp Phe Arg Ser Ile Ala Pro Ser Ile Ile Thr His
                405                 410                 415

Asn Val Ser Pro Asp Thr Leu Asn Arg Glu Gly Cys Lys Glu Tyr Asp
            420                 425                 430

Val Ala Pro Gln Val Gly His Arg Phe Cys Lys Asp Phe Pro Gly Phe
        435                 440                 445

Ile Pro Ser Leu Leu Gly Asp Leu Leu Glu Glu Arg Gln Lys Ile Lys
    450                 455                 460

Lys Lys Met Lys Ala Thr Ile Asp Pro Ile Glu Arg Lys Leu Leu Asp
465                 470                 475                 480

Tyr Arg Gln Arg Glu Ile Lys Ile Leu Ala Asn Ser Tyr Tyr Gly Tyr
                485                 490                 495

Tyr Gly Tyr Ala Arg Ala Arg Trp Tyr Cys Lys Glu Cys Ala Glu Ser
        500                 505                 510

Val Thr Ala Trp Gly Arg Glu Tyr Ile Thr Met Thr Ile Lys Glu Ile
    515                 520                 525

Glu Glu Lys Tyr Gly Phe Lys Val Ile Tyr Ser Asp Thr Asp Gly Phe
            530                 535                 540

Phe Ala Thr Ile Pro Gly Ala Asp Ala Glu Thr Val Lys Lys Lys Ala
545                 550                 555                 560

Met Glu Phe Leu Lys Tyr Ile Asn Ala Lys Leu Pro Gly Ala Leu Glu
                565                 570                 575

Leu Glu Tyr Glu Gly Phe Tyr Lys Arg Gly Phe Phe Val Thr Lys Lys
        580                 585                 590

Lys Tyr Ala Val Ile Asp Glu Glu Gly Lys Ile Thr Thr Arg Gly Leu
    595                 600                 605

Glu Ile Val Arg Arg Asp Trp Ser Glu Ile Ala Lys Glu Thr Gln Ala
            610                 615                 620

Arg Val Leu Glu Ala Leu Leu Lys Asp Gly Asp Val Glu Lys Ala Val
625                 630                 635                 640

Arg Ile Val Lys Glu Val Thr Glu Lys Leu Ser Lys Tyr Glu Val Pro
                645                 650                 655

Pro Glu Lys Leu Val Ile His Glu Gln Ile Thr Arg Asp Leu Lys Asp
        660                 665                 670

Tyr Lys Ala Thr Gly Pro His Val Ala Val Ala Lys Arg Leu Ala Ala
    675                 680                 685

Arg Gly Val Lys Ile Arg Pro Gly Thr Val Ile Ser Tyr Ile Val Leu
            690                 695                 700

Lys Gly Ser Gly Arg Ile Gly Asp Arg Ala Ile Pro Phe Asp Glu Phe
705                 710                 715                 720

Asp Pro Thr Lys His Lys Tyr Asp Ala Glu Tyr Tyr Ile Glu Asn Gln
                725                 730                 735

Val Leu Pro Ala Val Glu Arg Ile Leu Arg Ala Phe Gly Tyr Arg Lys
        740                 745                 750

Glu Asp Leu Arg Tyr Gln Lys Thr Arg Gln Val Gly Leu Ser Ala Trp
    755                 760                 765

Leu Lys Pro Lys Gly Thr
```

770

<210> SEQ ID NO 2
<211> LENGTH: 2325
<212> TYPE: DNA
<213> ORGANISM: Artificial Sequence
<220> FEATURE:
<223> OTHER INFORMATION: Nucleotide sequence of wild-type KOD-type DNA
      polymerase

<400> SEQUENCE: 2

| | | | | | |
|---|---|---|---|---|---|
| atgattctgg | acaccgatta | catcaccgaa | gatggcaagc | cagttatccg | catttttcaaa | 60 |
| aaagagaatg | gtgaattcaa | gatcgaatat | gatcgtacct | tcgagccgta | cttctatgct | 120 |
| ctgctgaaag | acgatagcgc | gattgaggag | gtcaagaaaa | tcaccgcgga | gcgtcacggt | 180 |
| acggttgtta | ccgtgaaacg | cgtggagaaa | gtccagaaga | aatttctggg | tcgcccggtt | 240 |
| gaagtgtgga | agctgtactt | tacgcatccg | caagatgttc | cggcgattcg | cgataagatt | 300 |
| cgtgagcacc | cggcagtcat | tgacatctac | gagtatgaca | ttccgttcgc | caagcgttat | 360 |
| ctgatcgata | agggtctggt | cccgatggag | ggtgacgaag | aactgaagat | gctggcgttc | 420 |
| gccatcgcca | ctctgtacca | cgagggtgaa | gagtttgccg | agggtccgat | cttgatgatt | 480 |
| tcctacgcgg | acgaagaggg | cgcacgtgtt | atcacgtgga | aaaatgttga | tctgccgtat | 540 |
| gttgacgtcg | taagcaccga | gcgtgagatg | atcaaacgtt | ttctgcgcgt | tgttaaagaa | 600 |
| aaagatcctg | acgtgctgat | cacctacaac | ggtgacaatt | tcgatttcgc | gtacctgaag | 660 |
| aaacgttgcg | aaaaactggg | tattaacttc | gcgctgggtc | gcgatggctc | tgaaccgaag | 720 |
| atccagcgca | tgggtgatcg | ttttgcggtc | gaggtgaagg | gtcgcattca | tttcgacctg | 780 |
| tacccggtga | ttcgtcgtac | catcaacttg | ccgacttaca | ccctggaagc | cgtctatgaa | 840 |
| gctgtatttg | gtcaaccgaa | agaaaaagtg | tacgctgagg | aaattacgac | ggcgtgggaa | 900 |
| accggtgaga | acctggagcg | cgttgcacgt | tattctatgg | aggacgcgaa | agttacctac | 960 |
| gaactgggta | agagttcct | gccgatggag | gcccaactgt | cccgtctgat | cggccaaagc | 1020 |
| ctgtgggacg | ttagccgcag | cagcaccggt | aacttagttg | aatggttctt | gctgcgtaag | 1080 |
| gcatacgaac | gcaatgagct | ggcgccgaac | aaaccggacg | agaaagaatt | ggcgcgtcgc | 1140 |
| cgccagagct | atgagggtgg | ttatgtcaaa | gaaccggagc | gcggcttgtg | ggagaacatc | 1200 |
| gtctatttgg | attttcgtag | cattgcaccg | agcatcatta | tcacgcataa | tgtgagcccg | 1260 |
| gatacgttga | atcgtgaggg | ctgtaaggaa | tacgacgtgg | cgcctcaggt | tggccaccgt | 1320 |
| ttctgcaagg | actttccggg | ctttatcccg | agcctgctgg | gtgatttgct | ggaggaacgt | 1380 |
| cagaaaatca | agaagaagat | gaaagcaacc | attgatccga | tcgagcgcaa | attactggac | 1440 |
| taccgtcaac | gtgaaatcaa | gatcctggcg | aattcgtatt | atggttacta | tggctacgcg | 1500 |
| cgtgcgcgct | ggtattgcaa | agagtgtgcc | gagagcgtga | ccgcttgggg | tcgtgagtac | 1560 |
| attaccatga | cgatcaaaga | gattgaagag | aaatacggct | ttaaggttat | ctatagcgac | 1620 |
| accgacggtt | tctttgcaac | tatccctggc | gcagacgcag | aaaccgttaa | gaaaaaggca | 1680 |
| atggagtttc | tgaagtatat | caacgcgaag | ttgccaggcg | ccctggaact | ggagtacgag | 1740 |
| ggcttctaca | gcgtggcttt | tttcgtgacg | aaaaagaaat | acgctgttat | tgatgaagag | 1800 |
| ggcaagatca | cgacccgtgg | cctggaaatt | gtgcgccgtg | attggagcga | aattgcaaaa | 1860 |
| gaaacgcaag | cgcgtgtgct | ggaagcgctc | ctgaaggacg | cgacgtcga | aaagctgtg | 1920 |
| cgtattgtta | agaggtcac | cgagaagctg | agcaaatacg | aggtcccgcc | agagaaattg | 1980 |

```
gtgattcacg aacagattac gcgtgacctg aaagactata aggccaccgg tccgcatgtc    2040
gcagtggcga agcgcctggc ggctcgcggt gtgaagatcc gtccgggtac cgtcattagc    2100
tatatcgtgc tgaagggcag cggtcgtatc ggcgaccgtg cgattccgtt cgacgaattt    2160
gatccgacca aacacaaata tgatgcggaa tactatattg agaaccaagt gctgccagcc    2220
gttgagcgta ttctgcgcgc cttcggttac cgcaaggaag atctgcgtta ccagaaaact    2280
cgtcaggtcg gtctgtccgc atggctgaaa ccgaagggca cctga                   2325

<210> SEQ ID NO 3
<211> LENGTH: 25
<212> TYPE: DNA
<213> ORGANISM: Artificial Sequence
<220> FEATURE:
<223> OTHER INFORMATION: Primer Cloning-F

<400> SEQUENCE: 3 ggtttttta tggggggagt ttagg                                            25

<210> SEQ ID NO 4
<211> LENGTH: 25
<212> TYPE: DNA
<213> ORGANISM: Artificial Sequence
<220> FEATURE:
<223> OTHER INFORMATION: Primer Cloning-R

<400> SEQUENCE: 4
catctcatct gtaacatcat tggca                                           25

<210> SEQ ID NO 5
<211> LENGTH: 37
<212> TYPE: DNA
<213> ORGANISM: Artificial Sequence
<220> FEATURE:
<223> OTHER INFORMATION: Primer P1A

<400> SEQUENCE: 5
cgtgtatgcg taataggatc ccgactcact atggacg                              37

<210> SEQ ID NO 6
<211> LENGTH: 37
<212> TYPE: DNA
<213> ORGANISM: Artificial Sequence
<220> FEATURE:
<223> OTHER INFORMATION: Primer P2A

<400> SEQUENCE: 6
cgtgtatcgt ccatagtgag tcgggatcct attacgc                              37
```

RECOMBINANT KOD POLYMERASE

TECHNICAL FIELD

The present disclosure relates to the field of biotechnology, specifically to a recombinant KOD polymerase.

BACKGROUND ARTS

The role of DNA polymerase is to replicate DNA quickly and accurately, which plays an important role in transmitting genetic information precisely and maintaining the stability of genetic material in living organism. There are five types of DNA polymerases in *Escherichia coli*, and according to the sequence homology of these DNA polymerases, they are divided into A, B, C and other types. The total folding structure of DNA polymerase is similar with that of human hand, which is divided into three parts: palm, thumb and finger. Although the structures of the fingers and palm domains of different types of DNA polymerases vary greatly, the palm domains for catalysis differ slightly. The major amino acid sequence of the active sites of DNA polymerase are conserved, but these conserved active sites are also relatively easy to change, and unnatural specific dNTPs can be incorporated to keep the activity of DNA polymerase from decreasing significantly (see U.S. Pat. No. 6,602,695 of Patel et al.).

KOD DNA polymerase belongs to B-family DNA polymerase, which can replicate DNA quickly and accurately. It is a heat-resistant DNA polymerase with a wide range of applications. One of the most important applications is in genome sequencing, such as SBS sequencing, which use nucleotides modified in the 3' sugar hydroxyl group to block the addition of other nucleotides. The use of nucleotides with 3' blocking groups allows the incorporation of nucleotides into the polynucleotide chain in a controlled manner. After the addition of each nucleotide, the presence of the 3' blocking group prevents other nucleotides from being incorporated into the chain. After removing the blocking group, the natural free 3' hydroxyl group is restored for adding the next nucleotide. However, there are many technical defects with current SBS sequencing, such as short read length of sequencing and slow reaction rate. KOD polymerase is an enzyme product specifically improved to address these technical defects by removing the 3'-5' exonuclease activity of wild-type KOD polymerase. A certain amount of optimized mutation sites were screened by computer simulation and prediction of the DNA binding region, dNTP catalytic site and other protein domains. Experimental screening of the mutated KOD polymerases yielded a batch of usable mutation site information, and it was found that the KOD polymerase can be modified by incorporating some unnatural amino acids. At present this type of products have been used in sequencing (see patent number of Liu Fen et al.).

DISCLOSURE OF THE PRESENT INVENTION

A purpose of the present invention is to provide a recombinant KOD polymerase.

The recombinant KOD polymerase provided by the present invention is a protein which is A) or B) as follows:

A) the protein shown is a protein that has DNA polymerase activity obtained by modifying amino acid residues in at least one of the 18 positions 675, 385, 710, 674, 735, 736, 606, 709, 347, 349, 590, 676, 389, 589, 680, 384, 496 and 383 of the amino acid sequence of wild-type KOD DNA polymerase;

B) the protein shown is a protein derived from A) that has DNA polymerase activity by adding a tag sequence to the end of the amino acid sequence of the protein shown in A).

In the protein as defined above, A) the protein shown is a protein that has DNA polymerase activity obtained by modifying amino acid residues in at least two of the following 18 positions 675, 385, 710, 674, 735, 736, 606, 709, 347, 349, 590, 676, 389, 589, 680, 384, 496 and 383 of the amino acid sequence of wild-type KOD DNA polymerase.

In the protein as defined above, A) the protein shown is a protein that has DNA polymerase activity obtained by modifying amino acid residues in at least three of the following 18 positions 675, 385, 710, 674, 735, 736, 606, 709, 347, 349, 590, 676, 389, 589, 680, 384, 496 and 383 of the amino acid sequence of wild-type KOD DNA polymerase.

In the protein as defined above, A) the protein shown is a protein that has DNA polymerase activity obtained by modifying amino acid residues in at least four of the following 18 positions 675, 385, 710, 674, 735, 736, 606, 709, 347, 349, 590, 676, 389, 589, 680, 384, 496 and 383 of the amino acid sequence of wild-type KOD DNA polymerase.

In the protein as defined above, A) the protein shown is a protein that has DNA polymerase activity obtained by modifying amino acid residues in at least five of the following 18 positions 675, 385, 710, 674, 735, 736, 606, 709, 347, 349, 590, 676, 389, 589, 680, 384, 496 and 383 of the amino acid sequence of wild-type KOD DNA polymerase.

In the protein as defined above, A) the protein shown is a protein that has DNA polymerase activity obtained by modifying amino acid residues in at least six of the following 18 positions 675, 385, 710, 674, 735, 736, 606, 709, 347, 349, 590, 676, 389, 589, 680, 384, 496 and 383 of the amino acid sequence of wild-type KOD DNA polymerase.

In the protein as defined above, the modification is amino acid substitution.

In the protein as defined above, the amino acid substitution is at least one of the following:

the alanine at position 675 is substituted with phenylalanine or methionine;

the glutamate at position 385 is substituted with methionine or tryptophan;

the isoleucine at position 710 is substituted with serine or histidine;

the lysine at position 674 is substituted with leucine or cysteine;

the asparagine at position 735 is substituted with histidine;

the glutamine at position 736 is substituted with glutamate or alanine;

the arginine at position 606 is substituted with histidine or methionine;

the arginine at position 709 is substituted with serine or histidine;

the serine at position 347 is substituted with isoleucine or methionine;

the threonine at position 349 is substituted with phenylalanine or isoleucine;

the threonine at position 590 is substituted with lysine or leucine;

the threonine at position 676 is substituted with lysine or tyrosine;

the valine at position 389 is substituted with isoleucine or methionine;

the valine at position 589 is substituted with histidine or glutamine;

the valine at position 680 is substituted with methionine or glutamate;

the tyrosine at position 384 is substituted with phenylalanine or tryptophan;

the tyrosine at position 496 is substituted with leucine or isoleucine;

the serine at position 383 is substituted with threonine.

In the protein as defined above, the amino acid sequence of wild-type KOD DNA polymerase is shown in SEQ ID NO: 1.

The protein shown in A) is a point mutant of KOD DNA polymerase, specifically a single point mutant of Table 1 in the examples or a multiple-point mutant of Table 2 in the examples.

A DNA molecule encoding the protein as defined above also falls within the scope of the present invention.

An expression cassette, recombinant vector, recombinant bacteria or transgenic cell line comprising the DNA molecule as defined above also falls within the scope of the present invention.

A use of the protein as defined above as a DNA polymerase also falls within the scope of the present invention.

Or the DNA molecule or the expression cassette, recombinant vector, recombinant bacteria or transgenic cell line as define above in the preparation of DNA polymerase falls within the scope of the present invention.

A use of the protein, the DNA molecule or the expression cassette, recombinant vector, recombinant bacteria or transgenic cell line as defined above in sequencing falls within the scope of the present invention; the sequencing as defined above is specifically DNA sequencing.

Or a use of the protein, the DNA molecule or the expression cassette, recombinant vector, recombinant bacteria or transgenic cell line as defined above in the preparation of products for sequencing in the preparation of products for sequencing.

In the use defined above, the product is a kit.

Based on the kinetic simulation and statistical inference of the KOD polymerase, the present invention obtains mutation sites that can be used for experimental screening. And experimental program was designed with semi-rational design, enzyme variant library construction and high-throughput screening to improve the catalytic, physical and chemical properties of polymerase and develop DNA polymerases suitable for DNB sequencing attached to the chip surface. Finally, the recombinant DNA polymerases were isolated and purified.

THE MOST PREFERABLE EMBODIMENT TO IMPLEMENT THE INVENTION

The experimental methods used in the following examples are conventional methods unless otherwise specified.

The materials and reagents used in the following examples are commercially available unless otherwise specified.

Example 1. Preparation of KOD DNA Polymerase Mutant

In the present invention, the expression vectors comprising KOD DNA polymerase or mutants thereof was constructed using DNA 2.0 Electra™ Cloning Reagents Kit, and His tag was used for Ni column affinity purification.

1. Preparation of Wild-Type KOD DNA Polymerase

The amino acid sequence of wild-type KOD DNA polymerase is SEQ ID NO: 1 in Sequence Listing, and its coding gene sequence is SEQ ID NO: 2 in Sequence Listing.

(1) Construction of Wild-Type Expression Vector pD441-WT

The wild-type recombinant expression vector pD441-WT was obtained by recombining the gene encoding wild-type KOD DNA polymerase fused with His tag to vector pD441-pelB (DNA2.0, pD441-pelB) according to the operation steps of the instruction of Electra™ Cloning Reagents Kit (DNA2.0, pD441-pelB). The gene encoding wild-type KOD DNA polymerase fused with His tag was expressed using the signal peptide on vector pD441-pelB.

The nucleotide sequence of gene encoding wild-type KOD DNA polymerase fused with His tag was a sequence obtained by linking 6× His tag codons at the 3' end of SEQ ID NO: 2.

Figure 1:
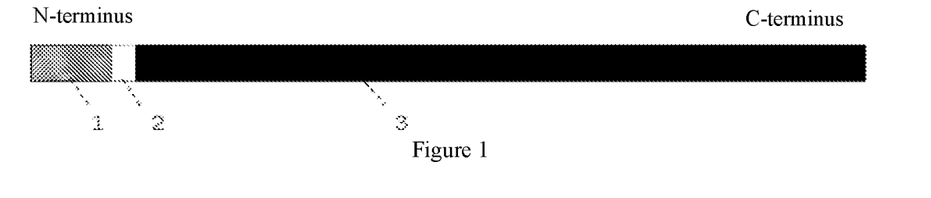
FIG. 1 shows a schematic diagram of the structure of recombinant KOD DNA polymerase.

The amino acid sequence of wild-type KOD DNA polymerase fusion protein was obtained by connecting 6× His tags with the [[C]]N-terminus of the amino acid of SEQ ID NO: 1, as shown in FIG. 1, wherein 1 represents the signal peptide pelB; 2 represents the purification tag His of fusion protein; 3 represents Wild-type KOD DNA polymerase.

(2) Construction of Recombinant Bacteria

The wild-type recombinant expression vector pD441-WT was transducted into E. coli BL21 competent cells (purchased from TransGen Biotech Co., Ltd.), and coated on a plate containing 50 µg/ml of kanamycin to select positive colonies. 3-5 positive colonies were selected and then identified with PCR using primers Cloning-F (SEQ ID NO: 3 in the Sequence Listing) and Cloning-R (SEQ ID NO: 4 in the Sequence Listing). A fragment with a size of 2800 bp, which is basically consistent with the predicted theoretical value, was obtained and determined as a positive clone by comparison of the sequencing results and named BL21/pD441-WT.

```
SEQ ID NO: 3: Cloning-F:
5'GGTTTTTTTATGGGGGGAGTTTAGG 3'

SEQ ID NO: 4: Cloning-R:
5'CATCTCATCTGTAACATCATTGGCA 3'
```

(3) Expression and Purification of Wild-Type KOD DNA Polymerase Fusion Protein

A single colony of BL21/pD441-WT was inoculated and cultured overnight in 50 ml LB liquid medium (containing Kan50 µg/ml) at 37° C. and 220 Rpm/min. Then the cultured bacteria solution was diluted 1:100 the next day and transferred to 1 L LB liquid medium (containing 50 µg/ml of Kan), then cultured in a shaker at 37° C. and 220 rpm/min to OD 600 of 0.5-0.8. Next, a 0.5 mM final concentration of IPTG was added to induce the expression of fusion proteins at 25° C. overnight, and the BL21/pD441-WT bacterial broth after induction was obtained. IPTG was not added to the bacterial broth of the blank control group.

BL21/pD441-WT bacterial broth was centrifuged at 8000 rpm/min for 10 minutes. Then supernatant was discarded, and pelleted cells were collected and resuspended in buffer (50 mM KPO$_4$, 500 mM NaCl, 10 mM imidazole, 5% Glycerol, pH 7.0) adding with PMSF at final concentration of 0.5 mM. Then the bacteria was broken by ultrasonic breaker, with a working time of 40 min, power 200 W, ultrasonic setting of 1 s stop 2 s and alarm temperature of 15° C. After sonication, the cell crusing solution was water bathed at 80° C. for 20 minutes, during which attention was paid to regular mixing so that the cell crushing solution was heated evenly. Then the solution was centrifuged at 12000 rpm/min and 4° C. for 30 min, the supernatant was filtered with a 0.22 μm filter membrane, and the filtrate was collected to obtain crude cell extract.

The crude cell extract was loaded at an appropriate flow rate for Ni column affinity chromatography (the prepacked column of affinity chromatography was HisTrap FF, 5 ml, 17-5255-01, GE healthcare), and the column was equilibrated with 5 CV buffer 1 after loading; then eluted with 5 CV 3% buffer 2 (50 mMKPO$_4$, 1M NaCl, 5% Glycerol, pH 7.0) followed by 5 CV 50% buffer 2, and the eluate of the Ni column affinity chromatography corresponding to the peak value equal to 100 mAU or higher was collected.

The eluate corresponding to the peak value equal to 100 mAU or higher was loaded at a certain flow rate for ion exchange chromatography (the prepacked column of ion exchange was HiTrap Q HP, 5 ml, 17-1154-01, GE healthcare), and the column was equilibrated with 5 CV buffer 2 after loading, linear eluted with 0% buffer 2→60% buffer 2, and the eluate of the ion exchange chromatography corresponding to the peak value equal to 100 mAU or higher was collected.

The eluate of the ion exchange chromatography corresponding to the peak value equal to 100 mAU or higher was gel chromatographed (the prepacked column of gel chromatography was HiPrepSephacryl S-100 HR, 26 mm, 17-1194-01, GE healthcare), first the column was washed with 3CV 20% ethanol, followed by 3CV with water; after being equilibrated with 3CV 100% buffer 3 (20 mM Tris, 200 mM KCl, 0.2 mM EDTA, 10% Glycerol, pH 7.4), the sample was loaded, then the column was eluted with 1.5CV buffer 3, and the eluate was collected as purified wild-type KOD DNA polymerase fusion protein.

Figure 2:
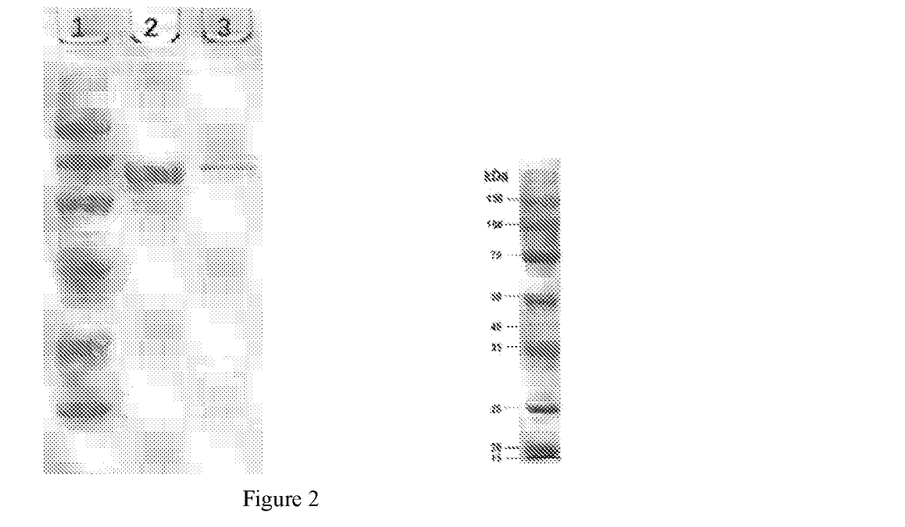
FIG. 2 shows the measurement of the purity of wild-type KOD DNA polymerase fusion protein.

The purified wild-type KOD DNA polymerase fusion protein was determinated by SDS-PAGE (5% stacking gel and 12% separation gel). The protein sample was mixed with SDS-PAGE protein loading buffer (5×), and treated at 95° C. for 5 min, and then loaded. The results are shown in FIG. 2. Lane 1 shows a protein Marker (PageRuler Prestained Protein Ladder, 26616, Thermo Scientific), lane 2 shows 10 μl of 1 mg/ml purified wild-type KOD DNA polymerase fusion protein, and lane 3 shows 10 μl of 0.05 mg/ml purified wild-type KOD DNA polymerase fusion protein that was diluted 20 times. It can be seen from the results of protein electrophoresis that the size of both proteins in lane 2 and lane 3 are about 91.5 KDa, which is consistent with the molecular weight reported in the literature.

The purity of the protein obtained by gel electrophoresis was analyzed with Quantity one software. The purity of the wild-type KOD DNA polymerase fusion protein after purification can reach 95% or more.

The target protein of approximately 91.5 KDa size can not be observed in uninduced BL21/pD441-WT bacterial broth.

In the control group, the vehicle pD441-pelB was introduced into *E. coli* BL21 to obtain BL21/pD441-pelB. The above method was used to express and purify the protein in the control group, but the target protein of about 91.5 KDa was not obtained.

2. Preparation of KOD DNA Polymerase Mutant Fusion Protein

KOD DNA polymerase mutant (the amino acid sequence is sequence A) was the protein obtained by modifying amino acid residues in at least one of the positions 675, 385, 710, 674, 735, 736, 606, 709, 347, 349, 590, 676, 389, 589, 680, 384, 496 and 383 of the amino acid sequence of wild-type KOD DNA polymerase; if there is only one amino acid substitution, a single point mutant of KOD DNA polymerase is obtained, if there are two amino acid substitutions, a two-point combination mutant of KOD DAN polymerase, if there are three amino acid substitutions, a three-point combination mutant of KOD DNA polymerase is obtained, and other mutants are obtained by analogy.

A gene encoding KOD DNA polymerase mutant (the nucleotide sequence is sequence B) was the nucleotide sequence obtained by mutating at least one amino acid codon of the gene encoding wild-type KOD DNA polymerase (SEQ ID NO: 2) according to positions 675, 385, 710, 674, 735, 736, 606, 709, 347, 349, 590, 676, 389, 589, 680, 384, 496 and 383 in SEQ ID NO: 1.

KOD DNA polymerase mutants can be obtained by site-directed mutagenesis in wild-type KOD DNA polymerase, or by other existing methods.

(1) Preparation of Recombinant Vector Expressing KOD DNA Polymerase Mutant

The recombinant vectors expressing different KOD DNA polymerase mutants were the vectors obtained by recombining different genes encoding KOD DNA polymerase mutant proteins fused with His tag into the vector pD441-pelB, and genes encoding different point mutant proteins fused with His tag were expressed using the signal peptide on the vector pD441-pelB.

The amino acid sequence of each KOD DNA polymerase mutant fusion protein was obtained by connecting 6× His tags to the N-terminus of the KOD DNA polymerase mutant shown in sequence A; wherein sequence A is the sequence obtained by mutating the amino acid sequence of wild-type KOD DNA polymerase as shown in SEQ ID NO: 1.

The nucleotide sequence of those genes encoding different KOD-type DNA polymerase mutant proteins fused with His tag were obtained by connecting codon of 6× His tag to the 3' end of different KOD DNA polymerase mutant proteins shown in sequence B; wherein sequence B is the sequence obtained by mutating the corresponding amino acid codon on the nucleotide sequence encoding wild-type KOD DNA polymerase as shown in SEQ ID NO: 2.

Single-point mutants are taken as an example below, as shown in Table 1.

Table 1 shows the mutation position and mutation information of single-point mutant KOD DNA polymerase

| Name of KOD DNA polymerase mutant | Mutation position (position in SEQ ID NO: 1) | The original amino acid of wild-type KOD DNA polymerase | The amino acid of KOD DNA polymerase mutant |
|---|---|---|---|
| A01 | 500 | A | D/G |
| A03 | 675 | A | F/M |
| B05 | 385 | E | M/W |
| A06 | 664 | E | L/M |
| C14 | 710 | I | S/H |
| D20 | 674 | K | L/C |
| D21 | 351 | N | Y/H |
| E23 | 735 | N | H |
| F29 | 736 | Q | E/A |
| G32 | 606 | R | H/M |
| H37 | 709 | R | S/H |

-continued

| Name of KOD DNA polymerase mutant | Mutation position (position in SEQ ID NO: 1) | The original amino acid of wild-type KOD DNA polymerase | The amino acid of KOD DNA polymerase mutant |
|---|---|---|---|
| I40 | 347 | S | I/M |
| J46 | 349 | T | F/I |
| K50 | 590 | T | K/L |
| L52 | 676 | T | K/Y |
| M54 | 389 | V | I/M |
| N56 | 589 | V | H/Q |
| O60 | 680 | V | M/E |
| P63 | 384 | Y | F/W |
| Q66 | 496 | Y | L/I |
| R69 | 383 | S | T |

Multiple-point mutants are taken as an example of KOD DNA polymerase, as shown in Table 2 below.

(2) Construction of Recombinant Bacteria

Using the same method of expression and purification as defined in step (2) of the preceding Item 1, the recombinant vector expressing different KOD type DNA polymerase mutants prepared in preceding program 1 was transducted into BL21 to obtain recombinant bacteria expressing different KOD DNA polymerase mutant fusion proteins.

(3) Expression and Purification of Mutants

The recombinant bacteria expressing different KOD DNA polymerase mutant fusion proteins prepared in the preceding step (2) were expressed and purified using the same method as that of wild-type KOD DNA polymerase fusion protein in the preceding Item 1 to obtain different KOD DNA polymerase mutat fusion proteins.

The different KOD DNA polymerase mutant fusion proteins were determined by SDS-PAGE (the stacking gel was 5% and the separation gel was 12%), and the target proteins were obtained. The purity of those proteins in the protein gel after electrophoresis was analyzed with Quantity one software, and it was found that the purity of all the different KOD DNA polymerase mutant fusion proteins can reach 95% or more.

Example 2. Testing the Properties of Recombinant KOD DNA Polymerase Mutant Fusion Proteins 1. Detection of Polymerase Activity of Recombinant KOD DNA Polymerase Mutant Fusion Proteins The polymerase activity was measured according to the method of Nishioka, M., et al. (2001. J. Biotechnol. 88), and one unit of enzyme activity is defined as the amount of acid-insoluble substances generated by polymerizing 10 nmol of dNTP by one unit enzyme in a 50 μl reaction system at 75° C. for 30 min.

The reaction solution was: 20 mM Tris-HCl (pH7.5), 8 mM $MgCl_2$, 50 μg/ml BSA, 0.15 mM each dNTPs (dATP, dTTP, dCTP and dGTP), [methyl-3H]-TTP (0.13 mCi/nmol, final concentration, (company MPBIO-FINE, product catalog number CB2272108), 150 mg/ml activated calf thymus DNA (company SIGMA-ALDRICH, product catalog number GE27-4575-01), 7.5 mM DTT, 1 μL wild-type KOD DNA polymerase (1 mg/ml), the total reaction volume was 50 μl.

The reaction solution was reacted at 75° for 30 minutes, and then the polymerase activity of wild-type KOD DNA polymerase calculated according to the definition of enzyme activity was 2 U/μl.

Wild-type KOD DNA polymerase fusion proteins and KOD DNA polymerase mutant fusion proteins are taken as examples to perform the polymerization reaction as defined above.

Wherein, the KOD DNA polymerase mutants are the multiple-point mutants of KOD DNA polymerase in Table 2: AB60, AB70, AB71, CD72, CD73, EF74, EF75, EF76, GH77 and GH78;

Table 2 shows the multiple-point mutants of KOD DNA polymerase

| Name | Polymerase activity |
|---|---|
| WT (wild-type KOD DNA polymerase) | 2.0 |
| AB60 | 2.5 |
| AB70 | 3.1 |
| AB71 | 3.3 |
| CD72 | 2.8 |
| CD73 | 2.4 |
| EF74 | 2.7 |
| EF75 | 3.5 |
| EF76 | 3.2 |
| GH77 | 3.8 |
| GH78 | 4.5 |

The specific mutation positions and methods of mutants shown in Table 2 are as follows:

the amino acid sequence of AB60 is that the arginine at position 709 of SEQ ID NO: 1 is mutated to serine, and the valine at position 589 of SEQ ID NO: 1 is mutated to histidine;

the amino acid sequence of AB70 is that the threonine at position 676 of SEQ ID NO: 1 is mutated to lysine, the valine at position 589 of SEQ ID NO: 1 is mutated to histidine, and the valine at position 680 SEQ ID NO: 1 is mutated to methionine;

the amino acid sequence of AB71 is that the lysine at position 674 of SEQ ID NO: 1 is mutated to leucine, the valine at position 589 of SEQ ID NO: 1 is mutated to histidine, and the valine at position 680 of SEQ ID NO: 1 is mutated to methionine;

the amino acid sequence of CD72 is that the threonine at position 676 of SEQ ID NO: 1 is mutated to lysine, the valine at position 589 of SEQ ID NO: 1 is mutated to histidine, the valine at position 680 of SEQ ID NO: 1 is mutated to methionine, and the tyrosine at position 384 of SEQ ID NO: 1 is mutated to phenylalanine;

the amino acid sequence of CD73 is that the valine at position 389 of SEQ ID NO: 1 is mutated to isoleucine, the lysine at position 674 of SEQ ID NO: 1 is mutated to leucine, the valine at position 589 of SEQ ID NO: 1 is mutated to histidine, and the valine at position 680 of SEQ ID NO: 1 is mutated to methionine;

the amino acid sequence of EF74 is that the lysine at position 674 of SEQ ID NO: 1 is mutated to leucine, the valine at position 589 of SEQ ID NO: 1 is mutated to histidine, the valine at position 680 of SEQ ID NO: 1 is mutated to methionine, the serine at position 383 of SEQ ID NO: 1 is mutated to threonine, and the tyrosine at position 384 of SEQ ID NO: 1 is mutated to phenylalanine;

the amino acid sequence of EF75 is that the threonine at position 349 of SEQ ID NO: 1 is mutated to phenylalanine, the valine at position 589 of SEQ ID NO: 1 is mutated to histidine, the threonine at position 676 of SEQ ID NO: 1 is mutated to lysine, the valine at position 680 of SEQ ID NO: 1 is mutated to methionine, and the tyrosine at position 496 of SEQ ID NO: 1 is mutated to leucine;

The amino acid sequence of EF76 is that the valine at position 589 of SEQ ID NO: 1 is mutated to histidine, the threonine at position 676 of SEQ ID NO: 1 is mutated to lysine, the valine at position 680 of SEQ ID NO: 1 is mutated to methionine, the serine at position 383 of SEQ ID NO: 1 is mutated to threonine, and the tyrosine at position 384 of SEQ ID NO: 1 is mutated to phenylalanine;

The amino acid sequence of GH77 is that the valine at position 589 of SEQ ID NO: 1 is mutated to histidine, the threonine at position 676 of SEQ ID NO: 1 is mutated to lysine, the valine at position 680 of SEQ ID NO: 1 is mutated to methionine, the serine at position 383 of SEQ ID NO: 1 is mutated to threonine, the tyrosine at position 384 of SEQ ID NO: 1 is mutated to phenylalanine, and the arginine at position 709 of SEQ ID NO: 1 is mutated to serine;

The amino acid sequence of GH78 is that the valine at position 389 of SEQ ID NO: 1 is mutated to isoleucine, the valine at position 589 of SEQ ID NO: 1 is mutated to histidine, the threonine at position 676 of SEQ ID NO: 1 is mutated to lysine, the valine at position 680 of SEQ ID NO: 1 is mutated to methionine, the serine at position 383 of SEQ ID NO: 1 is mutated to threonine, and the tyrosine at position 384 of SEQ ID NO: 1 is mutated to phenylalanine.

The KOD DNA polymerase mutant fusion proteins were prepared by adding 6× His tags to the N-terminus of each KOD DNA polymerase mutant.

The results of the activity of KOD DNA polymerase mutant fusion proteins are shown in Table 2. It can be seen that the KOD DNA polymerase mutants have polymerase activity.

The polymerase activity results of other mutants were similar.

2. Kinetics of Single Base Incorporation of KOD DNA Polymerase Mutant Fusion Proteins In this example, dATP (dATP-Cy3) labeled with Cy3 fluorescent dye and substrate (P/T-2Cy5) labeled with Cy5 fluorescent dye were used to detect the relative reaction rate of recombinant KOD DNA polymerase mutants using a microplate reader, so as to approximately depict the Michaelis-Menten curve of each mutant, and the specific experimental method is as follows:

The single-stranded primers P1A (sequence 5 in the sequence listing) and P2A (sequence 6 in the sequence listing) that were both labeled with 5' Cy5 fluorescent were mixed 1:1, then the mixture was kept at 65° C. for 10 minutes, and naturally cooled to room temperature. The obtained annealing product, i.e., the substrate P/T-2Cy5 labeled with Cy5 fluorescent dye, was stored at −20° C. in the dark.

Enzyme activity was detected by BioTek microplate reader. The reaction was carried out in 384-well plate (Corning black, clear bottom 384 plate), and the total volume of the reaction solution was 50 µl. The specific reaction system is as follows:

The reaction system is: 1 U KOD polymerase mutant fusion protein, 1 µM dATP-Cy3, 10 µM dTTP, 10 µM dCTP, 10 µM dGTP and substrate P/T-2Cy5. The experiment was performed with 8 concentration gradients of 0.1, 0.2, 0.5, 1, 2, 3, 4 and 6 µM. The buffer for enzymatic reaction is 20 mM Tris-HCl, 10 mM $(NH_4)_2SO_4$, 10 mM KCl and 2 mM $MgSO_4$ with pH 8.5@25° C.

Kinetic detection mode was used in the enzymatic reaction, and the data was recorded every 30 s. The parameters of measurement are:

| | |
|---|---|
| Extension | 530 nm |
| Emission | 676 nm |
| Reaction Temperature | 40° C. |
| Reaction time | 30 min |

After the reaction, the spreadsheet of data and curve of enzyme activity can be exported directly, and the reaction rate of the relative fluorescence value can be approximately calculated.

The reaction rate to the fluorescence value depends on the concentration of the substrate P/T-2Cy5, so the Km value of recombinant KOD DNA polymerase mutant, which corresponds to the concentration of the substrate when it reaches half of the maximum reaction rate, can be approximately determined by measuring the activity of the mutant under different concentrations of substrate P/T-2Cy5.

The wild-type KOD DNA polymerase fusion protein (KOD-WT) was used as a control.

Figure 3:
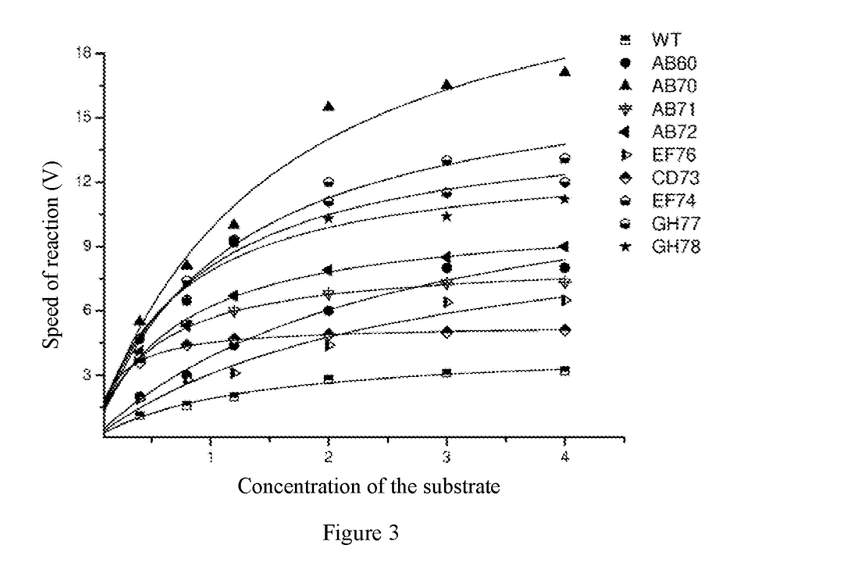
FIG. 3 shows the Michaelis-Menten curve of wild-type and recombinant KOD DNA polymerase fusion protein.

The Michaelis-Menten curves of KOD DNA polymerase mutant fusion proteins were shown in FIG. 3 and Table 3. It can be seen that the polymerase activity of KOD DNA polymerase mutants is higher than that of wild type. The specific experimental results can be referred to Table 3 below. The results of kinetic test of KOD DNA polymerase mutants showed that they had greater potential than wild type. In the sequencing process, the higher the catalytic efficiency of the enzyme reaction, the greater the value of Vmax/Km, which can speed up the reaction to a certain extent and shorten the time required for sequencing reaction. It can be seen from the experimental results that all the KOD DNA polymerase mutants have improved enzyme catalytic efficiency compared with the wild-type KOD DNA polymerase.

TABLE 3

Results of kinetic test of KOD DNA polymerase mutants

| Mutants | Vmax/km | Compare to WT (Vmax/km value of mutant to Vmax/km value of wild-type) |
|---|---|---|
| AB60 | 0.95E+07 | 2.7 |
| AB70 | 1.64E+07 | 4.7 |
| AB71 | 1.68E+07 | 4.2 |
| CD72 | 1.06E+07 | 3.9 |
| CD73 | 2.26E+07 | 6.5 |
| EF74 | 1.70E+07 | 6.2 |
| EF75 | 2.58E+07 | 7.5 |
| EF76 | 6.37E+06 | 2.5 |
| GH77 | 1.32E+07 | 3.4 |
| GH78 | 2.01E+07 | 7.3 |

INDUSTRIAL APPLICATION

The experiment of the present invention proves that aiming at further extending the read length of sequencing, shortening the reaction time and other improvement goals, the present invention further modified the KOD DNA polymerase based on the previous work, while protecting original functional sites involved in this area of the DNA polymerase B family to ensure they are still capable to complete the original basic functions. The recombinant KOD polymerase has higher reaction rate of DNA polymerase in sequencing and increased reaction read length. Compared with the wild-type DNA polymerase, the recombinant DNA polymerase exhibits better reaction rate, better affinity and other advantages in aspect of catalysis.

What is claimed is:

1. A protein, which is A) or B) as follows:
   A) a protein that has DNA polymerase activity obtained by substituting the following of wild-type KOD DNA polymerase:
      the valine at position 389 with isoleucine; the valine at position 589 with histidine; the threonine at position 676 with lysine; the valine at position 680 with methionine; the serine at position 383 with threonine; the tyrosine at position 384 with phenylalanine;
   B) a protein derived from A) that has DNA polymerase activity by adding a tag sequence to the end of the amino acid sequence of the protein shown in A);
   wherein the amino acid sequence of wild-type KOD DNA polymerase is shown in SEQ ID NO: 1.

2. A DNA molecule encoding the protein of claim 1.

3. An expression cassette comprising the DNA molecule of claim 2.

4. A method for preparing a DNA polymerase, comprising using the protein of claim 1 to prepare the DNA polymerase.

5. A method for sequencing, comprising using the protein of claim 1.

6. A recombinant vector comprising the DNA molecule of claim 2.

7. A recombinant bacteria comprising the DNA molecule of claim 2.

8. A transgenic cell line comprising the DNA molecule of claim 2.

9. A method for preparing a DNA polymerase, comprising culturing the recombinant bacteria of claim 7 so as to express a DNA polymerase; preferably further comprising purifying the DNA polymerase.

10. A method for preparing a DNA polymerase, comprising culturing the recombinant bacteria that obtained by transducting the recombinant vector of claim 6 so as to express a DNA polymerase; preferably the recombinant bacteria is BL21, more preferably further comprising purifying said DNA polymerase.

11. A method for sequencing, comprising using the DNA molecule of claim 2.

12. A method for preparing products for sequencing, comprising using the DNA molecule of claim 2.

* * * * *